United States Patent [19]

Suzuki

[11] Patent Number: 4,974,599
[45] Date of Patent: Dec. 4, 1990

[54] PORTABLE ELECTROCARDIOGRAPH

[75] Inventor: Takashi Suzuki, Soraku, Japan

[73] Assignee: Sharp Kabushiki Kaisha, Osaka, Japan

[21] Appl. No.: 426,786

[22] Filed: Oct. 25, 1989

[30] Foreign Application Priority Data

Oct. 25, 1988 [JP] Japan .............................. 63-268992
Oct. 25, 1988 [JP] Japan .............................. 63-268993
Oct. 25, 1988 [JP] Japan .............................. 63-268994
Oct. 25, 1988 [JP] Japan .............................. 63-268995
Oct. 25, 1988 [JP] Japan .............................. 63-268996

[51] Int. Cl.$^5$ .............................................. A61B 5/04
[52] U.S. Cl. ..................................... 128/696; 128/710
[58] Field of Search ............... 128/696, 710, 711, 712

[56] References Cited

U.S. PATENT DOCUMENTS 4,364,397 12/1982 Citron et al. ......................... 128/710
4,804,950 2/1989 Moon et al. ......................... 128/710
4,809,705 3/1989 Ascher ................................. 128/710
4,844,090 7/1989 Sekine ................................. 128/696
4,895,161 1/1990 Chudahy et al. .................... 128/696

Primary Examiner—Francis Jaworski
Assistant Examiner—George Manuel
Attorney, Agent, or Firm—Merchant, Gould, Smith, Edell, Welter & Schmidt

[57] ABSTRACT

A portable electrocardiograph which comprises a processing unit for outputting a display command signal for the display of an electrocardiographic wave, a display unit responsive to the display command to display the electrocardiographic wave, and a transparent touch panel assembly disposed above the display unit and having a pattern of scales defined thereon for facilitating a reading of the electrocardiographic wave displayed on the display unit.

5 Claims, 5 Drawing Sheets

Fig. 6
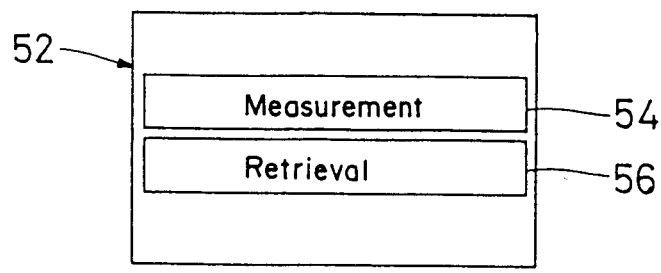
Fig. 7
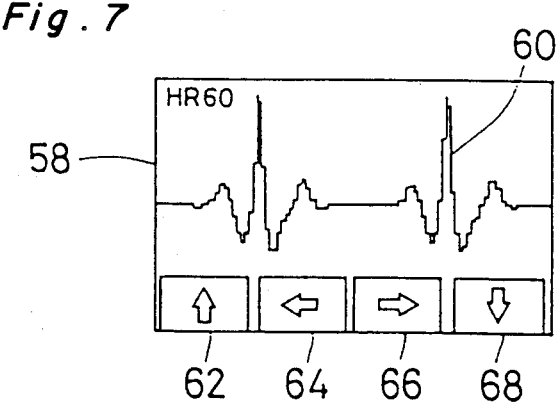
Fig. 8
| Sleeping | Sitting |
|---|---|
| Walking | Running |
| Exercising | Eating |
| Bathing | Evacuation |

Fig. 10A
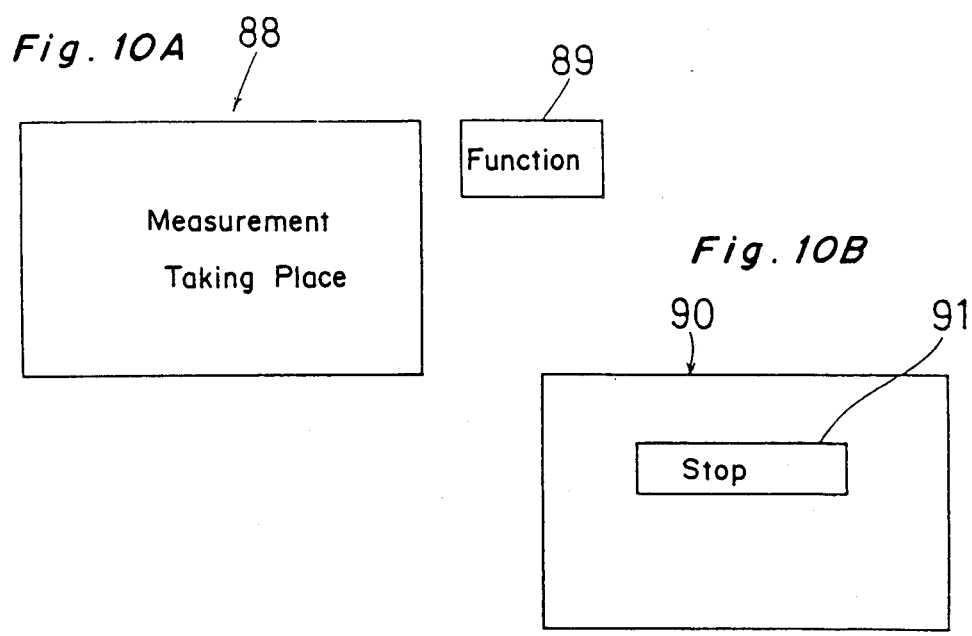
Fig. 10B
Fig. 11A
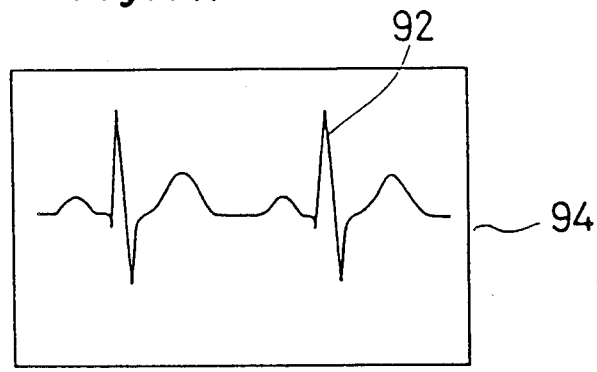
Fig. 11B
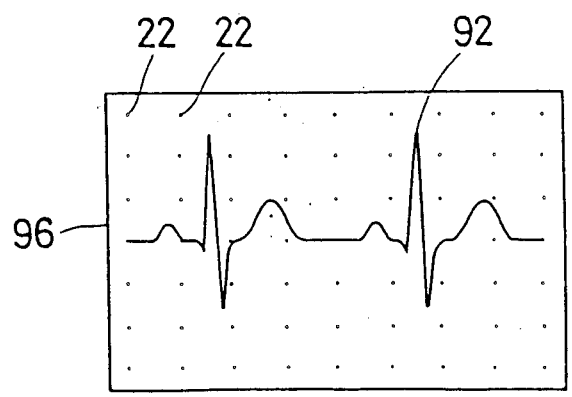

PORTABLE ELECTROCARDIOGRAPH

CROSS REFERENCE TO THE RELATED APPLICATION

U.S. Pat. application Ser. No. 324,082, filed Mar. 16, 1989, in the name of Takashi Suzuki.

BACKGROUND OF THE INVENTION

1. Field of the Invention

The present invention relates to a portable electrocardiograph capable of providing electrocardiographic data on a patient with no need to constrain the patient to the examination room.

2. Description of the Prior Art

The conventional electrocardiographic system comprises a display unit for the display of an electrocardiographic wave. The display unit used in combination or association with the electrocardiographic system is not provided with any calibrated scales which would facilitate a physician or technician to comprehend the size and/or movement of the electrocardiographic wave being displayed. The lack of the calibrated scales on the display unit has hitherto provided a problem in that a medical examination of the heart of a patient cannot be performed as correctly and quickly as possible with no difficulty.

The electrocardiographic system comprising a display unit employed in the form of a cathode ray tube (CRT), a keyboard having a plurality of input keys and a main body having a central processing unit built therein. In such prior art electrocardiographic system, some of the keys on the keyboards are required to be manipulated so that information concerning the type and level of a patient's symptom and a treatment can be inputted to the central processing unit. The manipulation of the keyboard for this purpose is not easy unless the physician or technician has an appropriate knowledge in addition to the knowledge of particulars in his or her major field of business.

Also, where an electrocardiographic recording is to be routinely made with the use of the electrocardiograph, the inputting of information connected with conditions under which an ECG measurement is carried out such as the type and level of the patient's subjective symptom and the pattern of behavior of a patient during the actual measurement appears to be feasible in that the accurate determination of the electrocardiogram so recorded can be accomplished. However, the prior art electrocardiographic system is of a construction comprising a main body which is separate from a main body of the electrocardiographic apparatus and which is provided with changeover switches generally equal in number to the possible number of the measurement conditions such as the number of patterns of behavior and the number of types of the subjective symptoms, a multi-event operating unit through which information connected with the pattern of behavior and the type of subjective symptom can be inputted to the main body, and a number of cords corresponding to the number of the changeover switches used for connecting the multi-event operating unit with the main body. Because of this, the prior art electrocardiographic system tends to be bulky in size enough to impose a load on a patient who is the user of the electrocardiographic system.

Moreover, in the prior art electrocardiographic system, a power switch, a start/stop switch and some other switches such as event markers are exposed to the outside, protruding outwardly from the casing. Therefore, where the prior art electrocardiographic system is transported, the patient carrying the system may erroneously manipulate one or more of the switches. Once one or more switches are erroneously manipulated during the measurement taking place, a loss of information recorded for a substantial length of time will take place.

SUMMARY OF THE INVENTION

The present invention has been devised with a view to eliminating the above discussed problems inherent in the prior art electrocardiographic apparatuses and has for its primary object to provide a portable electrocardiograph effective to permit the physician or technician to perform a quick and accurate examination of the state of the patient's heart with reference to the electrocardiographic wave displayed on a display unit.

Another important object of the present invention is to provide a portable electrocardiograph of the type referred to above, which can be handled easily by an operator less skilled in how to manipulate a keyboard input unit.

A further object of the present invention is to provide a portable electrocardiograph of the type referred to above, with which the ECG measurement appropriate to a particular condition which may vary depending on the pattern of behavior and the level of subjective symptom can be carried out efficiently and effectively.

A still further object of the present invention is to provide a portable electrocardiograph of the type referred to above, which is made compact in structure by eliminating the necessity of the main body to have complicated and various functions.

A still further object of the present invention is to provide a portable electrocardiograph of the type referred to above, wherein means is provided for avoiding any possible erroneous operation which may occur during the ECG measurement taking place or wherein means is provided for indicating that the operation of the electrocardiograph is interrupted once the erroneous operation takes place.

In order to accomplish the above described objects of the present invention, there is provided a portable electrocardiograph which comprises a processing unit for outputting a display command signal for the display of an electrocardiographic wave, a display unit responsive to the display command to display the electrocardiographic wave, and a transparent touch panel assembly disposed above the display unit and having a pattern of scales defined thereon for facilitating a reading of the electrocardiographic wave displayed on the display unit.

According to the present invention, the presence of the pattern of scales in the transparent touch panel assembly can facilitate a reading of the electrocardiographic wave displayed thereon.

In another preferred embodiment of the present invention, there is also provided a portable electrocardiograph which comprises a electrode means adapted to be attached to the skin of a living body for outputting an electrocardiographic signal, and a main body for processing the electrocardiographic signal supplied from the electrode means. The main body comprises a processing means responsive to the electrocardiographic signal from the electrode means and a keyed-in position signal supplied from a key-in input unit to perform a process of outputting various display commands according to a predetermined processing program, said display commands being used to display an electrocardiographic wave and key operating symbols on the basis of the electrocardiographic signal and the keyed-in position signal, respectively; a display unit operable in response to the display commands to display the electrocardiographic wave and the key operating symbols; and a transparent touch panel assembly disposed above the display unit and including the key-in input unit defined at a location where the key operating symbols are displayed, said touch panel assembly being operable to provide the keyed-in position signal to the processing means in response to a manipulation of the key-in input unit.

Thus, merely by depressing a portion of the transparent touch panel assembly which is encompassed by one of the key operating symbols, the keyed-in input can be readily accomplished.

Preferably, the main body may further comprise a storage unit for storing a processed output from the processing means and wherein said processing means is operable to cause the display unit to display the key operating symbols for inputting a condition of ECG measurement during the actual ECG measurement and also to cause the storage unit to store display commands corresponding respectively to the condition of ECG measurement and the electrocardiographic wave appropriate to such condition.

In this embodiment of the present invention, since during the actual ECG measurement the electrocardiographic wave appropriate to the particular measurement condition can be displayed on a screen at the display unit, the measurement conditions such as the pattern of behavior of the patient during the ECG measurement and the level of the subjective symptom can be displayed in terms of key operating symbols and, therefore, the necessity of use of complicated and bulky devices hitherto required for the recording and analysis of the electrocardiographic wave for each measurement condition can be advantageously eliminated.

Preferably, the key operating symbols may include, inter alia, a key operating symbol for avoiding any possible erroneous operation, and wherein the main body further comprises a function key which, when manipulated during an ECG measurement taking place, causes the key operating symbol for avoiding any possible erroneous operation to be displayed on the display unit.

In another preferred embodiment of the present invention, there is provided a portable electrocardiograph which comprises, in combination, a electrode means adapted to be attached to the skin of a living body for outputting an electrocardiographic signal, a main body for processing the electrocardiographic signal, supplied from the electrode means, and comprising a processing means responsive to the electrocardiographic signal from the electrode means and a keyed-in position signal supplied from a key-in input unit to perform a process of outputting various display commands according to a predetermined processing program, said display commands being used to display an electrocardiographic wave and key operating symbols on the basis of the electrocardiographic signal and the keyed-in position signal, respectively; a display unit operable in response to the display commands to display the electrocardiographic wave and the key operating symbols; and a transparent touch panel assembly disposed above the display unit and including the key-in input unit defined at a location where the key operating symbols are displayed, said touch panel assembly being operable to provide the keyed-in position signal to the processing means in response to a manipulation of the key-in input unit; and an IC card adapted to be removably loaded to the main body according to a particular application, said IC card comprising a storage unit for storing the predetermined processing program corresponding to contents of operation of the key-in input unit on the touch panel assembly, said predetermined processing program being adapted to be read out by the processing means.

Where the particular IC card is loaded in the main body of the electrocardiograph according to the present invention depending on a particular application, the contents of the key operating symbols displayed on the display unit can be altered and, therefore, a part of the function of the main body can be transferred to the IC card, making it possible to render the main body to be simple in structure and compact in size.

BRIEF DESCRIPTION OF THE DRAWINGS

These and other objects and features of the present invention will become clear from the following description taken in conjunction with a preferred embodiment thereof with reference to the accompanying drawings, in which:

FIG. 6 is a schematic diagram showing a menu displayed on a display window under one of modes of operation of the electrocardiograph;

FIG. 7 is a schematic diagram showing a data displayed as a result of a selection from the menu shown in FIG. 6;

FIG. 8 is a schematic diagram showing a different menu displayed on the display window for the selection of one of conditions under which the cardiographic measurement is carried out;

FIG. 10A and FIG. 10B are schematic diagrams showing displays effected on the display window for the purpose of avoiding any possible erroneous operation, respectively;

FIG. 11A is a schematic diagram showing a data display effected on the display window having no scale employed on the display window; and FIG. 11B is a diagram similar to FIG. 11A, showing the display window having dot scales.

DETAILED DESCRIPTION OF THE EMBODIMENT

Hereinafter, the present invention will be described in connection with a preferred embodiment thereof with reference to the accompanying drawings, particularly to FIGS. 1 to 4 which schematically illustrates an outer appearance of a portable electrocardiograph embodying the present invention, a display window assembly employed in the portable electrocardiograph, a layout of touch panel switches used in a transparent touch panel assembly in the electrocardiograph, and a portion of the transparent touch panel used in the electrocardiograph, respectively.

Figure 1:
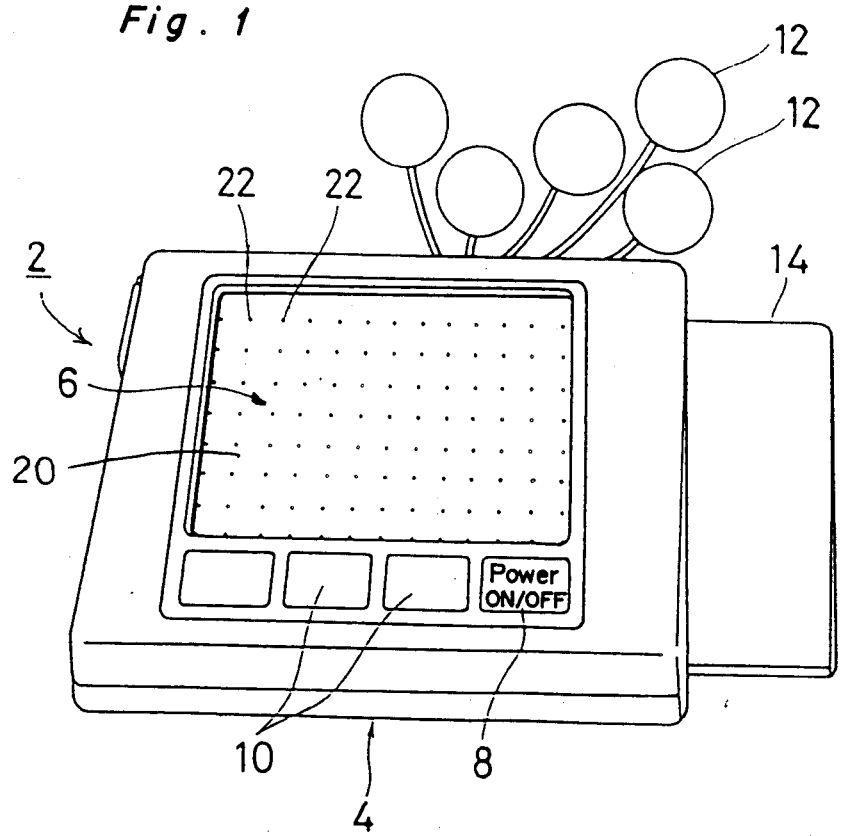
FIG. 1 is a schematic perspective view showing an outer appearance of a portable electrocardiograph embodying the present invention.
Figure 2:
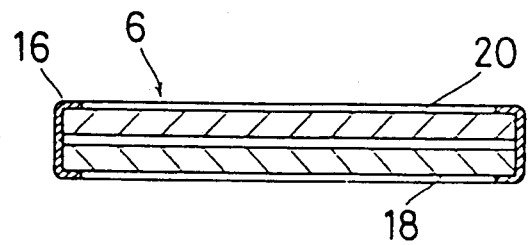
FIG. 2 is a schematic sectional view of a display window assembly employed in the portable electrocardiograph.

Referring first to FIGS. 1 and 2, the portable electrocardiograph generally identified by 2 comprises a main body 4 of generally flat rectangular configuration having a predetermined thickness and also having top and bottom major surfaces opposite to each other. The top surface of the main body 4 is formed with a generally rectangular display window assembly 6, delimited by a rectangular window frame 16 embedded therein, and also with a power control switch 8 and a plurality of other switches 10, all of these switches 8 and 10 being arranged in side-by-side relationship in a row extending below the display window assembly 6. The main body 4 has a plurality of cables or leads extending outwards from one of the four side faces of the main body 4 and terminating with corresponding electrode pieces 12 for attachment to various sites on the body of a patient so that cardiographic signals descriptive of the heart movements can be supplied to an electric circuitry built in the main body 4 as will be described later. The main body 4 also has a card slot defined in one of the side faces thereof for the insertion of one of a plurality of available IC cards into the main body 4.

The window frame 16 embedded in the main body 4 and delimiting the display window assembly 6 has mounted thereon a liquid crystal display unit 18 and a transparent touch panel 20 positioned above the liquid crystal display unit 18 as best shown in FIG. 2. The liquid crystal display unit 18 is operable to display an electrocardiographic wave and one or more key-operated legends. The transparent touch panel 20 is provided with dot scales 22 visible through the liquid crystal display unit 18, which dot scales are arranged in a matrix form comprising an array of rows and columns of dots. Each of these dot scales is defined by the tip of a corresponding one of generally elongated spacer pieces 30 as will be described in detail later.

Figure 4:
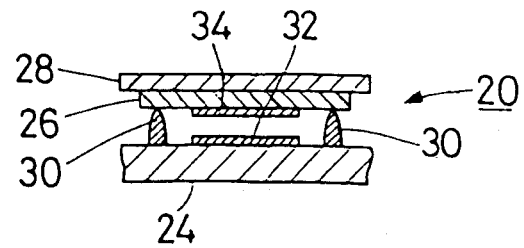
FIG. 4 is a schematic sectional view, on an enlarged scale, showing a portion of the transparent touch panel used in the electrocardiograph.
Figure 3:
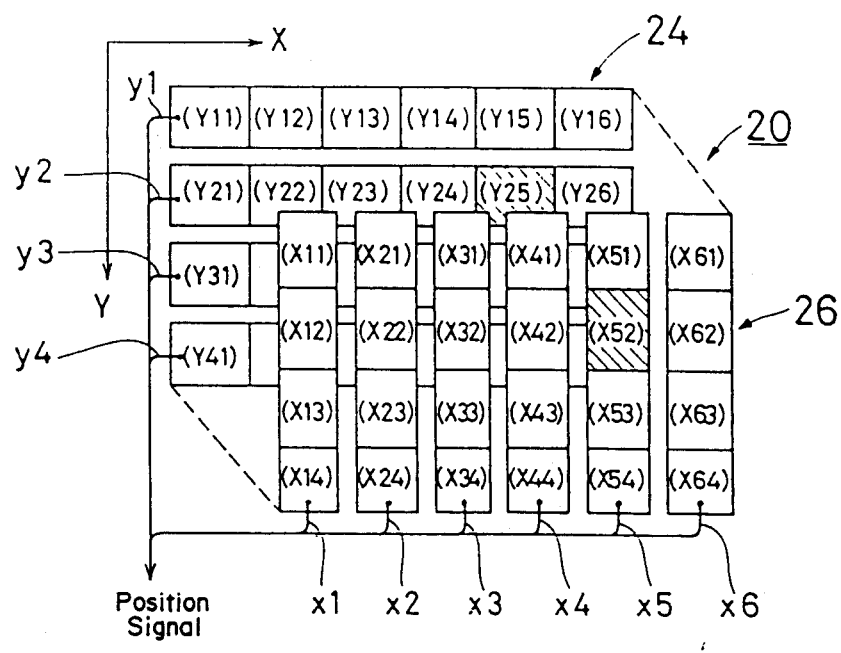
FIG. 3 is a schematic diagram showing a layout of touch panel switches used in a transparent touch panel assembly in the electrocardiograph.

Referring now to FIGS. 3 and 4 fragmentarily showing the details of the transparent touch panel 20, the touch panel 20 comprises generally rectangular transparent top and bottom plates 26 and 24 each made of, for example, a plate glass, which plates 26 and 24 are held spaced a predetermined slight distance from each other by means of the elongated spacer pieces 30 arranged in a matrix form as shown in FIG. 4. The transparent touch panel 20 also comprises a transparent protective film 28 coated on, or otherwise laid over, one of opposite surfaces of the top plate 26 remote from the bottom plate 24. As best shown in FIG. 3, the bottom plate 24 has defined therein a plurality of, for example, four, parallel rows of groups of regions, each of said rows extending in a direction generally parallel to a X-axis direction and each of said groups consisting of a plurality of, for example, six, regions that are generally designated by Y11 to Y16, Y21 to Y26, Y31 to Y36 or Y41 to Y46, respectively. Similarly, the top plate 26 has defined therein a plurality of, for example, six, parallel columns of groups of regions, each of said columns extending in a direction generally parallel to an Y-axis direction perpendicular to the X-axis direction and each of said groups consisting of a plurality of, for example, four, regions that are generally designated by X11 to X16, X21 to X26, X31 to X36, X41 to X46, X51 to X56 or X61 to X66, respectively. The four parallel rows of the six regions are electrically connected with each other and with an input circuit of a central processing unit, as will be described later, through respective signal lines x1 to x6, whereas the six parallel columns of the four regions are electrically connected with each other and with the input circuit of the central processing unit through respective signal lines y1 to y6.

The transparent touch panel 20 has an access surface accessible to a finger of an operator of the electrocardiograph, which access surface is divided into a plurality of surface areas distributed in a manner similar to the pattern of the regions in any one of the bottom and top plates 24 and 26. Therefore, when one of the surface areas of the touch panel 20, for example, the surface area aligned with the region X52 on the top plate 26 and with the region Y21 on the bottom plate 24, is depressed to allow an electrode in the region X52 to be brought into contact with an electrode in the mating region Y25, electric signals indicative of the position of such surface area can be inputted to the central processing unit 40 through the associated signal lines y2 and x5 as respective keyed-in position signals. Thus, assuming that the access surface of the transparent touch panel 20 represents a coordinate system, the keyed-in position signals generated from the transparent touch panel 20 consequent upon depression of a particular one of the surface areas of the transparent touch panel 20 are, when supplied to the central processing unit 40, recognized by the central processing unit 40 as a signal indicative of a particular point in such coordinate system, which point is, for the purpose of the present invention, generally expressed by (Xab, Ymn) wherein each of a and n represents an integer within the range of 1 to 6 and each of b and m represents an integer within the range of 1 to 4.

FIG. 4 illustrates a sectional representation, on an enlarged scale, of a portion of the transparent touch panel 20 at any arbitrarily chosen surface area thereof, that is, any point (Xab, Ymn) in coordinate system. The top and bottom plates 26 and 24 are kept spaced apart from each other by means of the generally elongated spacer pieces 30 arranged in a matrix form in correspondence with the division of the access surface of the transparent touch panel 20 into the surface areas. Respective tips of said spacer pieces 30 are visible through the top plate 26 and define the dot scales 22 arranged in a matrix form as shown in FIG. 1. Reference numeral 32 represents a transparent electrode foil deposited on the bottom plate 24 within each of the regions in each column and reference numeral 34 represents a mating transparent electrode foil deposited on the top plate 26 within each of the regions in each row so as to confront the associated electrode foil 32.

While the transparent touch panel 20 is of the construction as hereinbefore described, it will readily be understood that the transparent touch panel 20 provides a function of an input keyboard through which the operator of the portable electrocardiograph can enter commands to be supplied to the central processing unit 40. More specifically, when one of the surface areas of the touch panel 20 which represents a particular point (Xab, Ymn) in coordinate system is depressed, the electrode foil 34 on the top plate 26 which is aligned with such one of the surface areas of the touch panel 20 and the mating electrode foil 32 on the bottom plate 24 which is also aligned with such one of the surface areas of the touch panel 20 are brought into contact with each other to complete an electric circuit therebetween thereby to provide the corresponding keyed-in position signals to the central processing unit 40 which subsequently recognizes that the surface area of the touch panel 20 representative of the point (Xab, Ymn) in coordinate system has been depressed.

Figure 5:
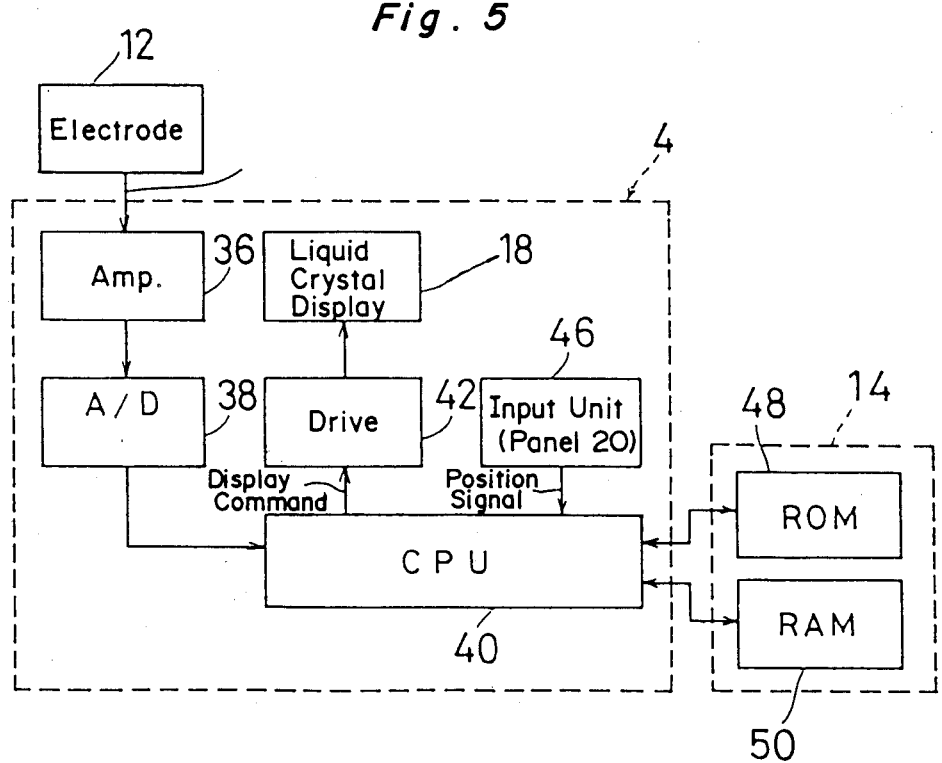
FIG. 5 is a schematic block circuit diagram showing a control system used in the electrocardiograph.

FIG. 5 illustrates an electric circuit accommodated within the main body 4, which is shown as connected with the electrodes pieces 12 and an IC card 14. The electric circuit accommodated within the main body 4 comprises an amplifier 36 for amplifying a cardiographic signal supplied from the electrode pieces 12, an analog-to-digital converter 38 for converting the amplified cardiographic signal into a digital cardiographic signal, the central processing unit 40 operable to perform various functions in dependence on the digital cardiographic signal supplied from the analog-to-digital converter 38, a drive circuit 42 operable in response to a display command from the central processing unit 40 to drive the liquid crystal display unit 18, and a keyboard input unit 46 which is comprised of the power switch 8, the various switches 10 and the paired electrode foils 32 and 34 deposited respectively on the bottom and top plates 24 and 26.

The IC card 14 comprises a read-only memory 48 and a random access memory 50 both built therein. The read-only memory 48 stores various programmed data such as formulas necessary for the central processing unit 40 to perform a process of compiling and formulating a cardiogram based on the electrocardiographic signal and also to analyze the heart movements in reference to the cardiogram. The random access memory 50 is used to store electrocardiographic signals provided from the central processing unit 40.

Hereinafter, the operation of the central processing unit 40 will be discussed.

After the electrode pieces 12 are attached to the examination sites on the body of a patient and the IC card 14 is loaded in the main body 4 of the electrocardiograph 2, the power switch 12 is turned on to power the electrocardiograph 2. Consequent upon the powering of the electrocardiograph 2, the central processing unit 40 generates a display command according to a program stored in the read-only memory 48 to drive the liquid crystal display unit 44 through the drive circuit 42 so that a screen 52 of a mode selection menu such as shown in FIG. 6 can appear on the display window assembly 6 in the main body 4.

As shown in FIG. 6, the mode selection menu screen 52 includes two elongated key-position defining blocks 54 and 56 which read "MEASUREMENT" and "RETRIEVAL". The legend in the block 54 speaks of a menu item querying the operator if he or she wishes to start the cardiographic measurement while the legend in the block 56 speaks of a menu item querying the operator if he or she wishes to retrieve contents stored in the random access memory 50 in the IC card 14. At the same time, each of the blocks 54 and 56 defines a key position to be keyed in by the operator. Therefore, when a portion of the mode selection menu screen 52 encompassed by, for example, the "MEASUREMENT" block 54 is manually depressed by the application of a finger pressure, the electrode foils 32 and 34 on the bottom and top plates 24 and 26 of the touch panel 20, which are encompassed by such block 54, can be electrically connected together. Consequent upon the electric connection between the electrode foils 32 and 34, the central processing unit 40 receives from the keyboard input unit 46 (i.e., the touch panel 20) the position signal representative of the point in coordinate system corresponding to such particular electrode foils 32 and 34, which have been connected together, and reads from the read-only memory 48 a program associated with the start of electrocardiographic measurement so that the central processing unit 40 can perform necessary functions.

On the other hand, when another portion of the mode selection menu screen 52 encompassed by the "RETRIEVE" block 52 is manually depressed by the application of a finger pressure, the electrode foils 32 and 34 on the bottom and top plates 24 and 26 of the touch panel 20, which are encompassed by such block 56, can be electrically connected together and, consequent upon the electric connection between the electrode foils 32 and 34, the central processing unit 40 receives from the keyboard input unit 46 the position signal representative of the point in coordinate system corresponding to such particular electrode foils 32 and 34, which have been connected together, and operates to read from the random access memory 50 a cardiographic wave stored in such memory 50 and, at the same time, to cause the selection menu 52 to disappear so that a screen 58 displaying the electrocardiographic wave 60 can appear together with a row of four retrieve keys 62 to 68 displayed below the electrocardiographic wave 60 as shown in FIG. 7.

The retrieve keys 62 to 68 are generally similar to so-called "Cursor Move" keys used in a wordprocessor keyboard and includes an Up Move key 62 bearing a symbol " ↑ ", a Forward Move key 64 bearing a symbol "←", a Backward Move key 66 bearing a symbol "→" and a Down Move key 68 bearing a symbol " ↓ ". The Up and Down Move keys 62 and 68 are used to scroll the electrocardiographic wave 60 appearing on the screen 58 upwardly and downwardly, respectively, within the framework of the screen 58 while the Forward and Backward Move keys 64 and 66 are used to scroll the electrocardiographic wave 60 appearing on the screen 58 rightward and leftward, respectively, within the framework of the screen 58 to enable the operator to view earlier and recent portions of the electrocardiographic wave 60 relative to that portion of the electrocardiographic wave 60 which is currently displayed.

Considering that the electrocardiogram may show a waveform variable depending on the condition under which the electrocardiogram is given, that is, the condition under which the ECG measurement is carried out, and in order for the operator to be capable of making a diagnosis as correctly as possible in reference to the electrocardiographic wave 60, the central processing unit 40 used in the practice of the present invention is so designed and so tailored that such a screen 70 as shown in FIG. 8 can be displayed, including a plurality of, for example, eight, key-position defining blocks which bear respective legends "SLEEPING", "WALKING", "EXERCISING", "BATHING", "SITTING", "RUNNING", "EATING" and "EVACUATION". As can readily be understood from these legends, the key-position defining blocks bearing the legends "SLEEPING", "WALKING", "EXERCISING", "BATHING", "SITTING", "RUNNING", "EATING" and "EVACUATION" are adapted to be depressed when the ECG measurement is carried out while the patient is lying on a bed; when the ECG measurement is carried out while the patient is walking; when the ECG measurement is carried out while the patient is taking exercise; when the ECG measurement is carried out while the patient is taking a bath; the ECG measurement is carried out while the patient is sitting; while the patient is running; when the ECG measurement is carried out while the patient is eating; and when the ECG measurement is carried out while the patient is evacuating, respectively. These conditions under which the ECG measurement is carried out and information concerning the electrocardiogram associated with each measurement condition are stored in the random access memory 50 built in the IC card 14 and can be called from the central processing unit 40 and, at the same time, displayed on the display window assembly 18, when the keyboard input unit 46 is manipulated. Accordingly, according to the illustrated embodiment of the present invention, the ECG measurement appropriate to a particular measurement condition can be carried out readily with no need to connect the main body with multi-input operating devices through cords depending on complex patterns of behaviors and subjective symptoms.

Figure 9A:
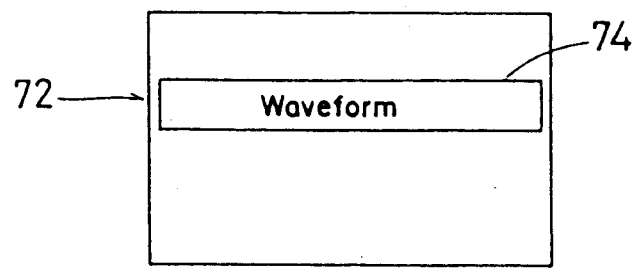
FIG. 9A, FIG. 9B and FIG. 9C are schematic diagrams showing different menu displayed on the display window when different IC cards are inserted in the electrocardiograph, respectively.
Figure 9B:
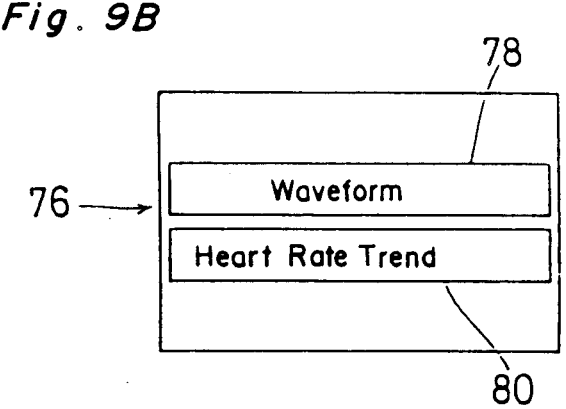

According to the illustrated embodiment of the present invention, arrangement has been made that different IC cards 14 one for a particular application can be selectively loaded into the main body 4. For example, where the first IC card 14 having the random access memory 50 which stores only electrocardiograms is loaded in the main body 4, and when the "MEASUREMENT" block 54 in the menu selection screen 52 shown in FIG. 6 is subsequently depressed, a screen 72 including a key-position defining block which bears a legend "WAVEFORM" as shown in FIG. 9A appears, thereby providing the operator with information that, in the event that the "WAVEFORM" block 74 is subsequently depressed, the electrocardiograph can be brought into a waveform display mode during which the electrocardiograms can be displayed. Where the second IC card 14 having the random access memory 50 which stores both of the electrocardiograms and heart beat trends is loaded in the main body 4, and when the "RETRIEVE" block 56 in the menu selection screen 52 shown in FIG. 6 is subsequently depressed, a screen 76 including key-position defining blocks 78 and 80 which bear respective legends "WAVEFORM" and "HEAT BEAT TREND" as shown in FIG. 9B appears, thereby providing the operator with information that, in the event that the "WAVEFORM" block 78 or the "HEAT BEAT TREND" block 80 is subsequently depressed, the electrocardiograph can be brought into the waveform display mode referred to above or a heart beat trend display mode, respectively.

Figure 9C:
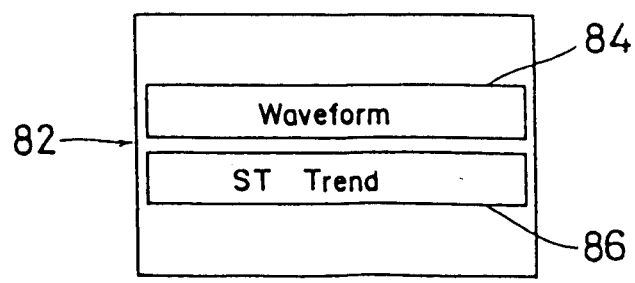

Again, where the third IC card 14 having the random access memory 50 which stores both of the electrocardiograms and ST trends is loaded in the main body 4, and when the "RETRIEVE" block 56 in the menu selection screen 52 shown in FIG. 6 is subsequently depressed, a screen 82 including key-position defining blocks 84 and 86 which bear respective legends "WAVEFORM" and "ST TREND" as shown in FIG. 9C appears, thereby providing the operator with information that, in the event that the "WAVEFORM" block 84 or the "ST TREND" block 86 is subsequently depressed, the electrocardiograph can be brought into the waveform display mode referred to above or a ST trend display mode, respectively.

It is to be noted that the random access memory 50 built in the IC card 14 is so designed and so tailored that, when the position signal is inputted from the keyboard input unit 46 to the central processing unit 40, the electrocardiogram recorded for 15 minutes before and after the position signal has been so inputted, results of real-time analysis of the electrocardiogram so recorded, an electrocardiogram recorded from an anomalous portion of the heart where the result of analysis indicates the presence of an anomalism in the heart, and/or the heart beat rate per beat can be recorded in the random access memory 50.

FIGS. 10A and 10B illustrate different manners of display effected in the liquid crystal display unit according to the present invention. In particular, while FIG. 10A illustrates a screen 88 bearing a legend "MEASUREMENT TAKING PLACE", a function key 89 for avoiding any possible erroneous operation is provided in the main body 4 at a location laterally of the screen 88 as shown therein. In order to avoid any possible interruption of the measurement which may occur when the power switch 8 is turned off during the ECG measurement taking place, when the function key 89 is depressed while the legend "MEASUREMENT TAKING PLACE" is displayed on the screen 88 as shown in FIG. 10A, the screen 88 supersedes such a screen 90 as shown in FIG. 10B, which screen 90 includes a key-in position defining block 91 bearing a legend "STOP". Only when this "STOP" block 91 in the screen 90 is subsequently depressed, the measurement can be interrupted. Accordingly, the interruption of the measurement then taking place can be enabled only when and after the function key 89 has been depressed during the display of the screen 90 followed by a depression of the "STOP" block 91 on the screen 90 and, therefore, any possible erroneous manipulation of the electrocardiograph during the transportation thereof can be avoided effectively. It is to be noted that, a predetermined time after the display of the legend "STOP" in the block 91, the screen 88 shown in FIG. 10A can be automatically resumed.

FIG. 11A illustrates a screen 94 of the electrocardiographic wave 92 appearing on the display unit 18, whereas FIG. 11B illustrates a screen 96 of the electrocardiographic wave 92 which corresponds to the screen 94 on the display unit 18 as viewed through the transparent touch panel 20. As can be understood from FIG. 11B, since in the illustrated embodiment the dot scales 22 defined by the elongated spacer pieces in the transparent touch panel 20 are viewable, the reading of the electrocardiographic wave can be facilitated. By way of example, it is a general practice for a physician or technician to read the displayed electrocardiogram with each unit of 10 mm in a vertical direction of the display screen taken as representing 1 mV and each unit of 25 mm in a horizontal direction of the same display screen taken as representing 1 second. Considering this, if the screen has no scale as shown in FIG. 11A, the physician or technician may have difficulty in reading the electrocardiographic wave displayed. However, the presence of the dot scales on the screen as shown in FIG. 11B can facilitate a quick reading of the displayed electrocardiographic wave. Where a diagnosis is to be made by enlarging the electrocardiographic wave displayed or by comparing different portions of the electrocardiographic wave displayed, the reading of the electrocardiographic wave can be further facilitated. As hereinbefore described, the dot scales viewable through the top plate 26 and the protective film 28 of the transparent touch panel 20 in the display window assembly 6 are defined by respective tips of the elongated spacer pieces 30 used to keep the top and bottom plates 26 and 24 spaced apart from each other.

Although the present invention has fully been described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

I claim:

1. A portable electrocardiograph which comprises:
   processing means for outputting a display command signal for the display of an electrocardiographic wave;
   a display unit responsive to the display command to display the electrocardiographic wave; and
   a transparent touch panel assembly located above and in partial contact with the display unit and having a pattern of scales defined thereon for facilitating a reading of the electrocardiographic wave displayed on the display unit beneath the transparent touch panel assembly.

2. A portable electrocardiograph which comprises electrode means adapted to be attached to the skin of a living body for detecting and outputting an electrocardiographic signal produced by the living body, and a main body for processing the electrocardiographic signal supplied from the electrode means, said main body comprising:
   processing means responsive to the electrocardiographic signal from the electrode means and a keyed-in position signal supplied from a key-in input unit to perform a process for outputting various display commands according to a predetermined processing program, said display commands being used to display an electrocardiographic wave and key operating symbols on the basis of the electrocardiographic signal and the keyed-in position signal;
   a display unit operable in response to the display commands to display the electrocardiographic wave and the key operating symbols; and
   a transparent touch panel assembly located above the display unit and including the key-in input unit defined at a location where the key operating symbols are displayed, said touch panel assembly being operable to provide the keyed-in position signal to the processing means in response to a manipulation of the key-in input unit.

3. The portable electrocardiograph as claimed in claim 2, wherein the main body further comprises a storage unit for storing a processed output from the processing means and wherein said processing means is operable to cause the display unit to display the key operating symbols for prompting input of a condition of ECG measurement during the actual ECG measurement, and said processing means also being operable to cause the storage unit to store display commands corresponding to the condition of ECG measurement and the electrocardiographic wave appropriate to such condition.

4. The portable electrocardiograph as claimed in claim 2, wherein the key operating symbols include, inter alia, a key operating symbol for avoiding any possible erroneous operation, and wherein the main body further comprises a function key which, when manipulated during an ECG measurement, causes the key operating symbol for avoiding any possible erroneous operation to be displayed on the display unit.

5. A portable electrocardiograph comprising:
   electrode means adapted to be attached to the skin of a living body for detecting and outputting an electrocardiographic signal produced by the living body;
   a main body for processing the electrocardiographic signal supplied form the electrode means, said main body comprising a processing means responsive to the electrocardiographic signal from the electrode means and a keyed-in position signal supplied from a key-in input unit to perform a process of outputting various display commands according to a predetermined processing program, said display commands being used to display an electrocardiographic wave and key operating symbols on the basis of the electrocardiographic signal and the keyed-in position signal; a display unit operable in response to the display commands to display the electrocardiographic wave and the key operating symbols; and a transparent touch panel assembly located above the display unit and including the key-in input unit defined at a location where the key operating symbols are displayed, said touch panel assembly being operable to provide the keyed-in position signal to the processing means in response to a manipulation of the key-in input unit; and
   an IC card adapted to be removable loaded to the main body according to a particular application, said IC card comprising a storage unit for storing the predetermined processing program corresponding to contents of operation of the key-in input unit on the touch panel assembly, said predetermined processing program being adapted to be read out by the processing means.

* * * * *